United States Patent [19]

Flatland

[11] 4,177,564
[45] Dec. 11, 1979

[54] DENTAL HANDPIECE CONNECTOR

[76] Inventor: Lloyd P. Flatland, 15 Quisisana Dr., Kentfield, Calif. 94904

[21] Appl. No.: 887,864

[22] Filed: Mar. 20, 1978

[51] Int. Cl.² ............................................... A61C 1/10
[52] U.S. Cl. ...................................... 433/82; 433/126
[58] Field of Search ....................... 285/265; 32/26, 27

[56] References Cited

U.S. PATENT DOCUMENTS

| | | | |
|---|---|---|---|
| 2,442,033 | 5/1948 | Brantly et al. | 32/28 |
| 3,663,044 | 5/1972 | Contreres et al. | 285/265 |
| 3,915,482 | 10/1975 | Fletcher | 285/265 |
| 3,921,296 | 11/1975 | Harris | 32/27 |

*Primary Examiner*—Robert Peshock
*Attorney, Agent, or Firm*—Lothrop & West

[57] ABSTRACT

A dental handpiece connector is adapted to be inserted between a standard dental handpiece and a standard supply tube for the handpiece. The connector allows rocking movement of the handpiece about a transverse axis and also allows rotary movement of the handpiece about a longitudinal axis, while continuing a supply of air or air and water from the supply tube to the handpiece. There is a detent to establish a preferred rocking position of the handpiece relative to the connector.

7 Claims, 7 Drawing Figures

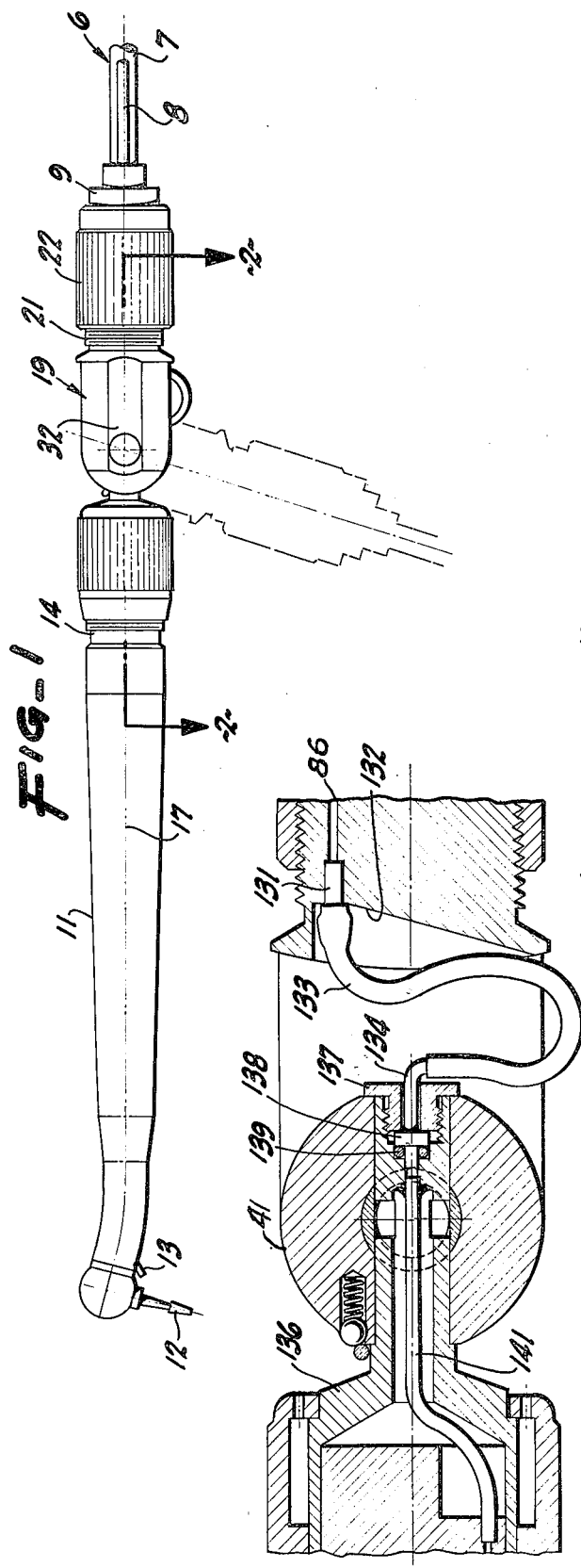
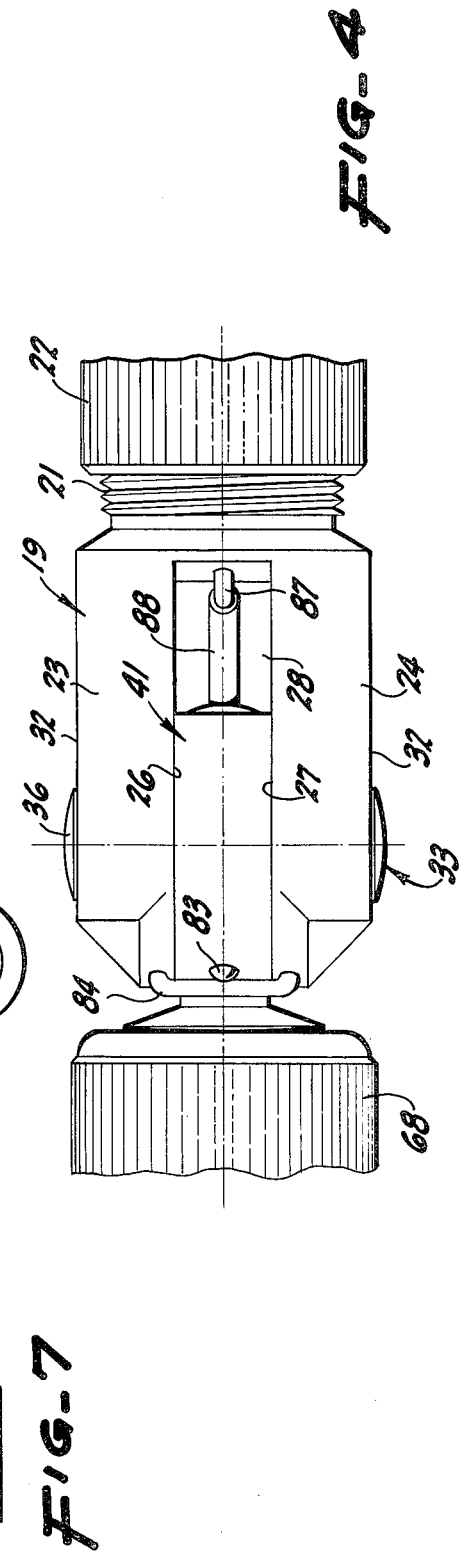

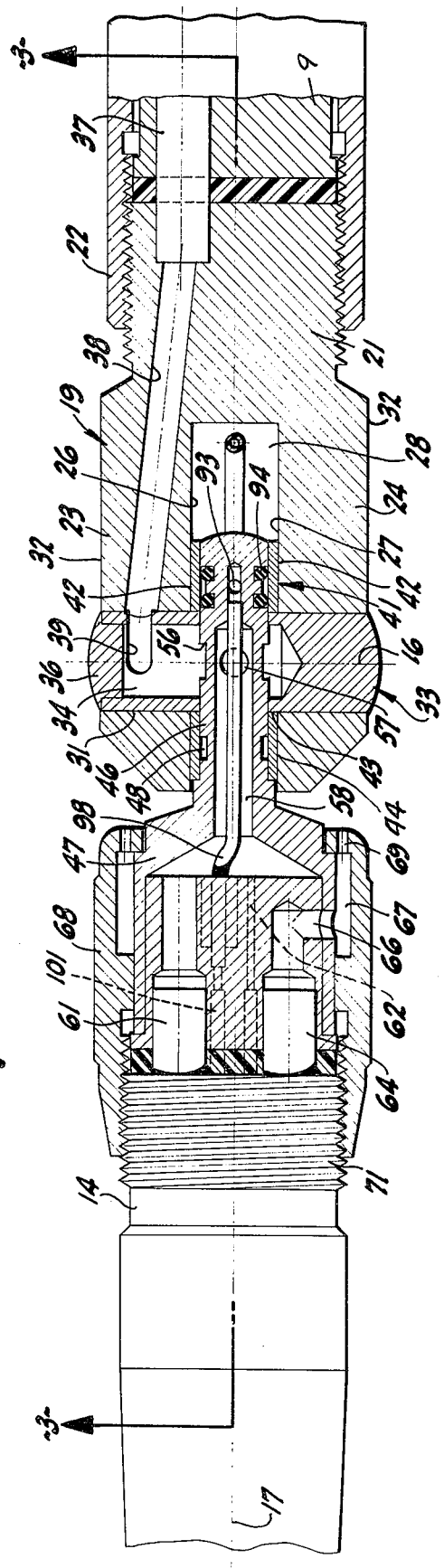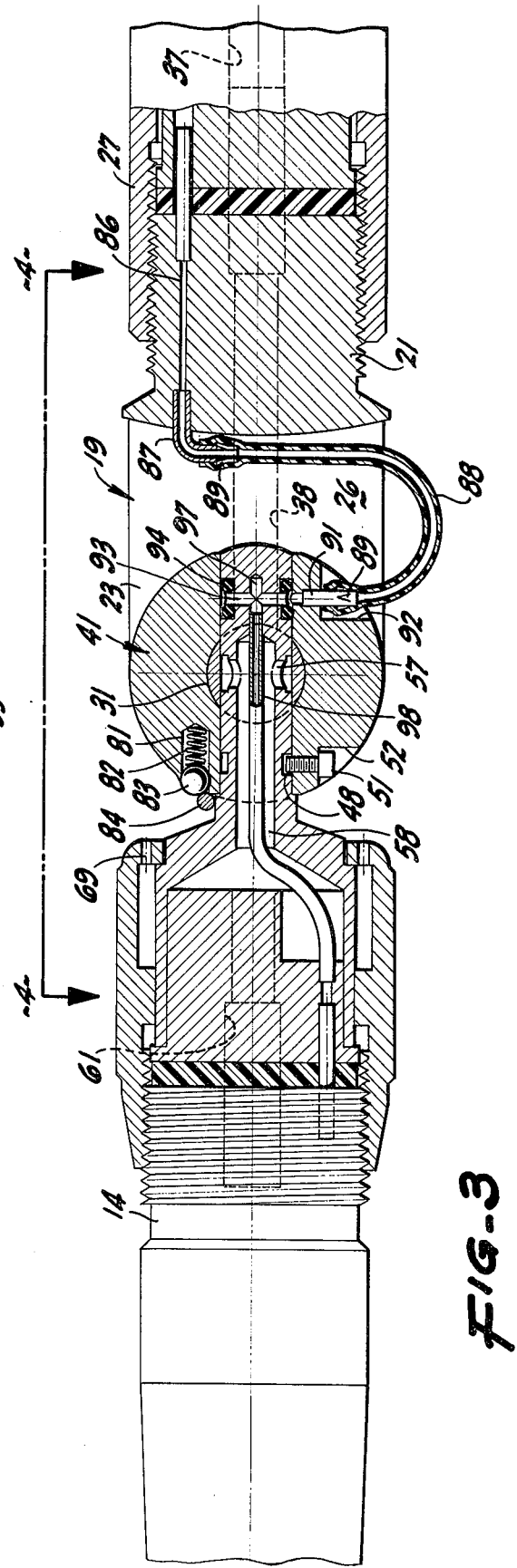

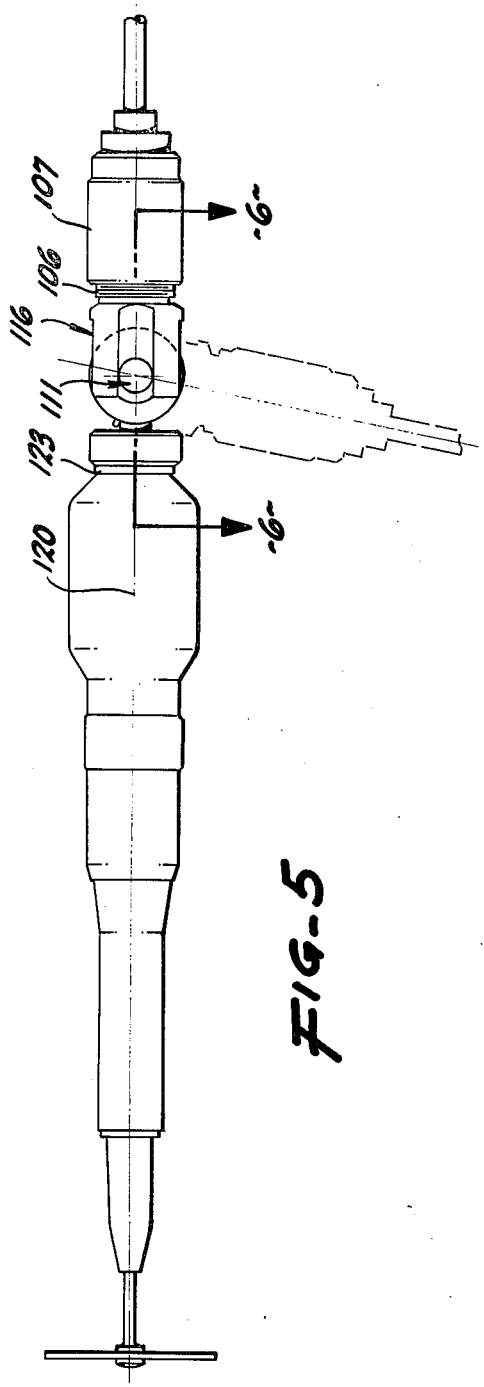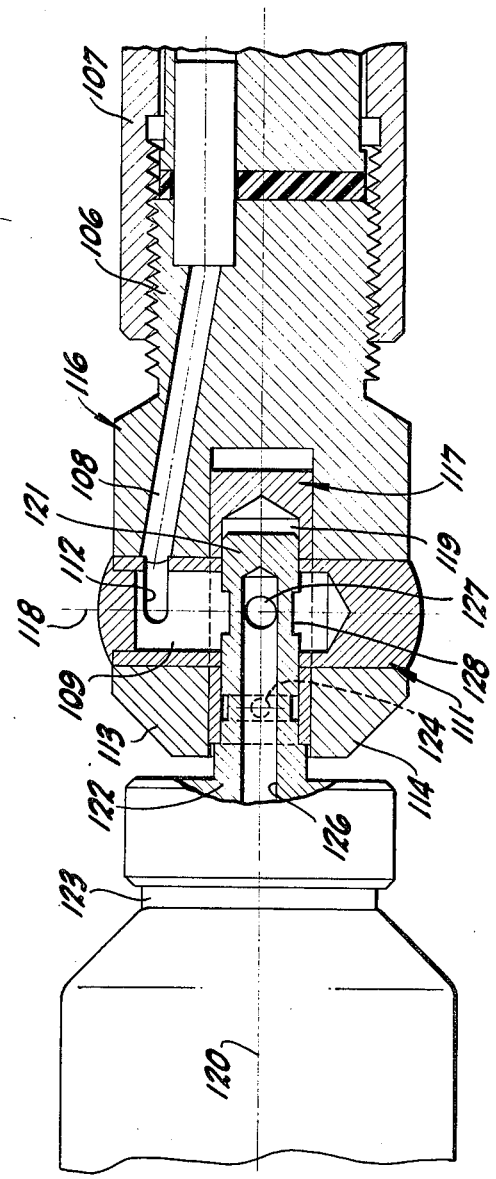

DENTAL HANDPIECE CONNECTOR

BRIEF SUMMARY OF THE INVENTION

In dental operations the handpiece is normally connected with fair rigidity to a supply hose for air and water utilized during the operation of the handpiece. The relative rigidity of the connection, and the fact that the hose may be somewhat stiff, is an extra burden for the dentist and after a long period of operation produces unusual and unreasonable fatigue in his hand and fingers. There is consequently provided an arrangement permitting the handpiece and the tube to have a great deal of additional flexibility, the handpiece being rotatable about its own longitudinal axis and also being rockable about a transverse axis, so that the degree of restraint imposed by the supply tube is very substantially reduced, and the dentist's accuracy is increased, while his fatigue is virtually eliminated. The arrangement includes a number of interconnected members to produce the desired relative motions and also to transmit the desired fluids such as air or air and water between the supply tube and the dental handpiece.

BRIEF DESCRIPTION OF THE SEVERAL VIEWS OF THE DRAWING

FIG. 1 is a side elevation, portions being broken away, of a dental handpiece connector constructed pursuant to the invention and shown in position between the normal supply tube and a standard handpiece.

FIG. 2 is a cross-section to an enlarged scale, the plane of section being indicated by the line 2—2 of FIG. 1.

FIG. 3 is a cross-section to the same scale as FIG. 2, the plane of section being taken on the line 3—3 of FIG. 2.

FIG. 4 is a plan of a portion of the connector, the view being indicated by the line 4—4 of FIG. 3.

FIG. 5 is a view like FIG. 1 but showing a modified form of dental handpiece connector.

FIG. 6 is a cross-section to an enlarged scale, the plane of section being indicated by the line 6—6 of FIG. 5.

FIG. 7 is a view like FIG. 3 but showing a modified form of tube connections.

DETAILED DESCRIPTION

The device can be embodied in a number of different forms, depending somewhat on the complexity of the surrounding dental equipment, but has been successfully incorporated in the forms shown herein. In one form, illustrated in FIGS. 1 through 4, the arrangement is for use with a standard dental supply line 6 that includes at least an air tube 7 and may also incorporate a water tube 8. These are standard and are terminated in a standard fitting 9. Normally this structure is connected more or less directly with a relatively standard dental handpiece 11 having arrangements for a dental tool 12 at one end, the tool being in this instance augmented by one or more jets 13 or nozzles. The handpiece includes an end fitting 14 of a standard nature.

In order to provide increased local flexibility not only about a transverse axis 16 (FIG. 2), but also about a longitudinal axis 17, there is provided an intermediate connector. The connector incorporates a metallic body 19 having a first base 21 threaded and adapted to be interengaged with a sleeve 22 also threaded and working with the fitting 9. The body 19 has a tine 23, usable alone or combined with a tine 24 making up a two-tined fork symmetrical with respect to the axis 17, generally circular in outside configuration and having a pair of internal, facing, planar surfaces 26 and 27, one on each tine and defining an internal cavity 28.

Symmetrical with the transverse axis 16 and extending entirely through the two tines 23 and 24 of the fork member 19 is a cross bore 31 opening onto outside flat surfaces 32 (FIG. 1). Adapted to seat in the cross bore 31 is a pin 33 symmetrical about the axis 16 and having an interior chamber 34 extending for much of the length of the pin but closed on one end by a plug 36.

Normally provided within the first connector or standard fitting is the end of a pressure air passage 37 having an extension in the fork body and continued by an air passage 38 opening into the cross bore 31. Communication is further established by a first opening 39 in the pin 33. In this way, a supply of working air or air under pressure is available within the interior chamber 34.

Disposed in the cavity 28 is a disc 41 having side faces 42 of a planar nature. If desired, only one side face need be used and then fits with free motion but virtually air-tight contact against one of the tine walls 26 and 27. As shown, both side faces 42 are in tight contact with both of the walls 26 and 27. The disc 41 is generally symmetrical about the axis 16 and has an axial passage 43 making a good journal fit with the pin 33, so that the disc and the pin are rotatable relative to each other about the axis 16. The disc has a radial passage 44 extending entirely therethrough, the passage being generally on the axis 17.

The radial bore 44 receives a cylindrical stem 46 extending coaxially from a second base 47. The stem 46 goes through the bore in the disc as well as through a similar bore in the pin 33 and is rotatable to an unlimited extent about the axis 17 relative to the fork member 19. The disc is kept in position partially by the positioning of the pin 33, and the stem 46 is kept in position in the disc by a special retaining mechanism. This includes a circular groove 48 around the stem and a retaining screw rod 51 threaded into a step 2 in the disc. The threaded screw 51 has a plain end that fits with designed tolerance in the groove 48. Removal of the screw 51 permits disassembly of this portion of the structure.

Air from the chamber 34 is conducted to the handpiece 11. For that reason, there is another groove 56 around the stem open to the chamber 34 and connected by apertures 57 to an interior conduit 58 in the stem and opening within the second base 47. Within the base, air from the conduit 58 can easily travel the customary main air passageway 61 to the turbine of the handpiece. If desired, a fraction of air from the conduit 58 can travel through a small, diversionary air passageway 62 (FIG. 2) through the dental handpiece 11 to emerge alongside of or at the nozzle 13 in the vicinity of the tool 12.

Air returning from the turbine travels through the customary passage 64 and then through an outlet duct 66 to a surrounding chamber 67 in a cap 68 having escape perforations 69 therein and itself in abutment with the second base 47. Since the cap 68 has an engagement by threads 71 with the handpiece, the entire handpiece portion of the assembly can be taken apart and put together quite easily. When it is together, there are adequate passageways appropriately connected together to carry air from the inlet tube 6 to the turbine or other driving mechanism and nozzle in the handpiece, during all of which the connector can swivel or rock about the transverse axis 16 and can rotate an unlimited amount about the longitudinal axis 17. This has the effect of lessening the load on the dentist and affords him much more freedom in manipulating the handpiece and relieves him of a good deal of strain and muscular tension that otherwise would occur.

It is sometimes the case that the amount of motion of the handpiece with respect to the remaining part of the structure should be limited or provided with some resistance to motion so as to maintain the handpiece, sometimes, in a straight-line or coaxial relationship with the fluid feeding structure especially for convenience in putting the device away in a dental unit or stand. If that is so, then there is provided in the disc 41 a socket 81 carrying a small coil spring 82 pressing against a captured detent ball 83 designed to cooperate with a staple 84 (FIG. 4) spanning the tines 23 and 24 of the fork member. The positions of the parts are such that, as shown in FIG. 3, the handpiece can be maintained in straight-line relationship with the fluid supply end of the structure. By overcoming the resistance of the spring 82, the staple 84 can move to the other side of the ball for free handpiece movement. In replacing the tool after use, the dentist can easily flick the handpiece into the straight-line position. The detent ball 83 engages the staple 84, so the straight-line position is maintained as the dentist restores the tube and handpiece to the dental stand or unit in normal rectilinear position.

Under some circumstances, there is a supply of water through the tube 8 that can appropriately be employed at the end of the handpiece. Under those circumstances, there is provided in the first base 21 and alongside the passageway 37 a connector channel 86 (FIG. 3) leading to a right-angle fitting 87 disposed in the cavity 28 and directed across the axis 17. Fastened to the fitting is a hose 88 held in position by sharp tabs 89. The hose is looped in the cavity, extends slightly outside the cavity, and then is engaged with a fitting 91 disposed in a step 92 in the disc and directed into a cross passageway 93 in the otherwise solid end of the stem. Leakage between the stem 46 and the disc 41 is precluded by O-rings 94.

Joined to a longitudinal bore 97 intersecting the cross passage 93 is a fitting 98 connected to the usual passage 101 (FIG. 2) in the handpiece and terminating in the nozzle 13. With this arrangement, the rotation of the handpiece about the axis 17 in an unlimited amount does not in any way interfere with the transmission of water therethrough by the mechanism described. Furthermore, rocking movement of the handpiece relative to the remaining part of the structure through a somewhat limited range about the axis 16 is entirely permissible because the hose 88 accommodates that movement without leakage. In this way there is provided a supply of water to a nozzle at the end of the handpiece during rotary movement and rocking movement of the parts.

Under some circumstances, the mechanism can be substantially simplified. As shown particularly in FIGS. 5 and 6, although some of the functions are not retained, the structure in general is somewhat less elaborate and is designed for different uses. In this case, the first base 106 is joined to a first connector 107 very much as before, with an air passage 108 extending into the interior chamber 109 of a cross pin 111 through a first opening 112. The cross pin is freely rotatable within the tines 113 and 114 of a fork member 116 and passes into and through a disc 117 rotatable around a cross axis 118 about which the pin is symmetrical. The disc has a bore 119 symmetrical about a longitudinal axis 120 and receives a stem 121 forming part of and projecting from a second base 122 secured to a second connector 123. The stem is retained for unlimited rotation about the axis 120 by a fastener 124 as before and has an axial or central bore 126 or air passageway. The air passageway communicates with the cavity 109 by means of a second opening 127 giving onto a circumferential groove 128 around the stem. In this fashion, a supply of air to run the handpiece turbine or the like is taken in from the customary source, is passed through the passageways despite their angular positions, so that the handpiece can be fully utilized without strain or extra load on the dentist's hand. Although a detent mechanism is not shown in the simplified version, it of course can be utilized in this environment as well.

In a modified form of tube connections as shown in FIG. 7, the general, surrounding construction is as shown in the FIG. 3 version. Instead of the right-angle fitting 87, there is provided a nipple 131 joined to the channel 86 and partly nested in a cutaway portion 132. A hose 133 is forced over the nipple and is looped to engage the transverse end of an elbow tube 134. A second base 136 is about like the second base 47 but is simplified. The groove 48 and the screw rod 51 are omitted. Rotary motion is allowed, but axial shifting is prevented by a flanged, hollow nut 137 in rotary abutment with the disc 41. The elbow tube 134 goes axially through the nut, being removably retained by the nut against a tube flange 138 abutting an O-ring 139. Beyond the flange, communication is into a tube 141 soldered into the disc 41 and connected in the same fashion as the fitting 98. The same flexibility is obtained as before with a simpler, less expensive mechanism.

In all forms of the device, there is provided a connector which can easily be adapted for use in presently existing supply lines and with presently existing handpieces and which reduces the load on the dentist's hand needed to provide rotation and rocking motion of the handpiece jacket.

I claim:

1. A dental handpiece connector for use with a dental air tube having a first connector thereon and with a dental handpiece having a second connector thereon, comprising a body having a first base adapted to engage said first connector and having a tine, means defining a cross bore in said tine, means in said body defining an air passage extending from said base to said cross bore, a disc adapted to be received against said tine, means defining an axial passage in said disc adapted to align with said cross bore, means defining a radial passage in said disc intersecting said axial passage, a pin having a pin chamber and arranged to confine said disc to rotation relative to said tine, means defining a first opening between the interior of said pin chamber and said air passage, a stem adapted to be received in said radial passage and having a second base adapted to engage said second connector, means defining a stem passageway in said stem, means defining a second opening between said stem passageway and said pin chamber, and means for confining said stem to rotation in said radial passage relative to said disc.

2. A device as in claim 1 in which said stem extends through said pin.

3. A device as in claim 1 in which said tine has a first planar surface and said disc has an opposite second planar surface in substantially air-tight, rotary abutment with said first planar surface.

4. A device as in claim 1 including means engaging said body and said disc and constituting a detent for relative rotary motion between said body and said disc.

5. A device as in claim 1 including a tube in said stem passageway, means defining a connector channel in said first base, and means including a hose joining said connector channel and said tube and in part disposed alongside said tine.

6. A device as in claim 1 including a main air passageway to said handpiece from said stem passageway and means defining a diversionary air passageway from said stem passageway to said handpiece.

7. A device as claim 1 including a second tine, said tine and said second tine being disposed on and in substantial contact with the opposite sides of said disc.

* * * * *